United States Patent [19]

Alper et al.

[11] Patent Number: 4,642,370

[45] Date of Patent: Feb. 10, 1987

[54] PROCESS FOR THE PRODUCTION OF CARBOXYLIC ACID ESTERS

[75] Inventors: Howard Alper, Ottawa, Canada; David J. H. Smith, Camberley, England; James B. Woell, Ottawa, Canada

[73] Assignee: The British Petroleum Company p.l.c., London, England

[21] Appl. No.: 713,910

[22] PCT Filed: Jul. 16, 1984

[86] PCT No.: PCT/GB84/00251

§ 371 Date: Mar. 14, 1985

§ 102(e) Date: Mar. 14, 1985

[87] PCT Pub. No.: WO85/00596

PCT Pub. Date: Feb. 14, 1985

[30] Foreign Application Priority Data

Jul. 16, 1983 [GB] United Kingdom ............... 8319291
May 25, 1984 [GB] United Kingdom ............... 8413369

[51] Int. Cl.$^4$ ............................................. C07C 69/76
[52] U.S. Cl. ...................................... 560/100; 560/103; 560/104; 560/105; 560/232; 562/406; 562/520

[58] Field of Search ............... 562/406, 520; 560/103, 560/106, 105, 100, 232

[56] References Cited

U.S. PATENT DOCUMENTS 3,116,306 12/1963 Heck .................................. 562/406
3,928,429 12/1975 El-Chahawi et al. ............... 562/406
4,034,004 7/1977 Cassar et al. ........................ 562/520

*Primary Examiner*—Paul J. Killos
*Attorney, Agent, or Firm*—Brooks Haidt Haffner & Delahunty

[57] ABSTRACT

Carboxylic acid esters are produced by reacting (i) carbon monoxide, (ii) a compound of the formula $M(OR)_x$ wherein M is either boron, silicon, aluminum, titanium or zirconium, x is the valency of M and R is a hydrocarbyl group and (iii) a hydrocarbyl halide, wherein the halide moiety is bromide, chloride or iodide, in the presence of a catalyst comprising one or more of the metals rhodium, iridium and cobalt in either elemental or compound form. When M is boron, silicon or aluminum and the halide moiety is chloride, there is preferably added a source of iodide.

13 Claims, No Drawings

PROCESS FOR THE PRODUCTION OF CARBOXYLIC ACID ESTERS

The present invention relates to a process for the production of carboxylic acid esters.

According to the present invention there is a provided a process for the production of a carboxylic acid ester which process comprises reacting (i) carbon monoxide, (ii) a compound of the formula $M(OR)_x$ wherein M is either boron, silicon, aluminium, titanium or zirconium, x is the valency of M and R is a hydrocarbyl group and (iii) a hydrocarbyl halide, wherein the halide moiety is bromide, chloride or iodide, in the presence of a catalyst comprising one or more of the metals rhodium, iridium and cobalt added in either elemental or compound form.

In the formula $M(OR)_x$ wherein M is either boron, silicon, aluminium, titanium or zirconium and x is the valency of M, the hydrocarbyl group may suitably be alkyl, aryl, aralkyl, cycloalkyl or substituted derivatives thereof. Preferably R in the aforesaid formula is alkyl, which is preferably a primary or a secondary alkyl. Examples of suitable R groups include —$C_2H_5$, —$CH(CH_3)_2$ and —$CH(CH_3)C_2H_5$. Preferably the metal M is boron, silicon or aluminium.

The hydrocarbyl moiety of the hydrocarbyl halide may suitably be an aromatic group, a benzylic group, an aliphatic group or a substituted derivative thereof and may be saturated or unsaturated. The halide moiety is either chloride, bromide or iodide, though the chlorides are preferably used in conjunction with compounds of the formula $M(OR)_x$ wherein M is of boron, silicon or aluminium when there is added an effective amount of a source of iodide. An amount suitable as an effective amount may be readily determined by those skilled in the art, but will usually be found to be of the order of that which is generally regarded as a catalytic amount. The source of iodide may suitably be iodine, an inorganic iodide or an organic iodide. Suitable inorganic iodides include the alkali metal iodides, of which potassium iodide is preferred. Suitable organic iodides include alkyl iodides, for example methyl iodide, and quaternary alkyl or aryl ammonium iodides. It will be appreciated that a source of iodide may be added with possible advantage when the halide moiety is bromide, though it is not essential for the effective working of the process. Examples of hydrocarbyl halides suitable for use in the process of the invention include benzyl bromide, benzyl chloride, para-methyl benzyl bromide, meta-methyl benzyl bromide, ortho-methyl benzyl bromide, para-fluoro benzyl bromide, 2-bromomethylnaphthalene, 1-bromomethylnaphthalene, bromobenzene and beta-bromostyrene.

Carbon monoxide is commercially available on a large scale and may be used without further purification. Alternatively, purified carbon monoxide may be employed. A wide range of carbon monoxide pressures may be used.

The catayIst comprises one or more of the metals rhodium, iridium and cobalt added in elemental or compound form. Preferably the metal is rhodium. Although the metal or metals may be employed in elemental form, preferably in a finally divided state, it is preferred to employ them in the form of soluble compounds. Suitable compounds include the salts of the metals, for example rhodium trichloride ($RhCl_3$), carbonyl complexes, for example $Rh(CO)_2Cl_2$ and organo compounds of the metals. Suitable organo compounds include dienyl metal complexes in which the dienyl moiety may be either linear or cyclic and either conjugated or non-conjugated, for example 1,5-hexadiene rhodium(I) chloride dimer. It is preferred, particularly when the hydrocarbyl halide reactant is an aromatic halide, for example a bromo-substituted benzene or naphthalene, to employ a bimetallic catalyst. Suitably the bimetallic catalyst comprises one of the metals rhodium, iridium and cobalt, preferably rhodium, and another metal selected from Group VIII of the Periodic Table of the elements as found in Advanced Inorganic Chemistry (2nd Edition) by F. A. Cotton and G. Wilkinson, of which palladium is preferred. It is also preferred to employ, as one component of the bimetallic catalyst, the metal in the form of a compound of a hydrocarbyl substituted phosphine, arsine or stibine. Typically, there may be employed in the reaction of an aromatic halide a catalyst comprising 1,5-hexadiene rhodium (I) chloride dimer and $Pd(PPh_3)_4$ wherein Ph represents phenyl.

A solvent may be employed if so desired. Suitable solvents include hydrocarbons, such as , for example paraffinic and aromatic hydrocarbons. Examples of suitable solvents include heptane, n-hexane, toluene, benzene and xylenes.

The process may suitably be operated at a temperature in the range 20° to 250° C., preferably 50° to 150° C. The reaction period for a batch reaction may be up to 72 hours, though shorter periods suitably in the range from 8 to 24 hours may be employed.

The process for the production of carboxylic acid esters, exemplified by the use of aluminium alkoxides, is believed to be represented by the following equation:

$$3RX + 3CO + Al(OR^1)_3 \rightarrow 3RCOOR^1 + AlX_3$$

wherein RX is an hydrocarbyl halide and $Al(OR^1)_3$ is an aluminium alkoxide as hereinbefore described.

The invention will now be illustrated by reference to the following Examples.

EXAMPLE 1

A mixture of 1,5-hexadienerhodium (I) chloride dimer (0.090 g; 0.11 mmol), $Al(OC_2H_5)_3$ (2ml) and benzyl bromide [$PhCH_2Br$] (2.0 mmol) was heated at 75° C. for about 15 h under carbon monoxide. The solution was then cooled. Ether (10 ml) and 1M NaOH (5 ml) were added and the resulting mixture was filtered through Celite. The filtrate was extracted three times with ether (in total 250 ml), the ether extract was dried over anhydrous magnesium sulphate and the ester product recovered.

Ethyl phenylacetate [$PhCH_2COOC_2H_5$] was obtained in 100% yield.

EXAMPLE 2

The procedure of Example 1 was repeated except that $Al(OC_2H_5)_3$ was replaced by $Al[OCH(CH_3)_2]_3$.

Isopropyl phenylacetate [$PhCH_2COOCH(CH_3)_2$] was obtained in 52% yield.

EXAMPLE 3

The procedure of Example 1 was repeated except that $Al(OC_2H_5)_3$ was replaced by $Al[OCH(CH_3)C_2H_5]_3$.

Sec-butyl phenylacetate [$PhCH_2COOCH(CH_3)C_2H_5$] was obtained in 68% yield.

EXAMPLE 4

The procedure of Example 1 was repeated except that benzyl bromide was replaced by p-methylbenzyl bromide [p-$CH_3C_6H_4CH_2Br$].

Ethyl p-methylphenylacetate [p-$CH_3C_6H_4CH_2COOC_2H_5$] was obtained in 63% yield.

EXAMPLE 5

The procedure of Example 1 was repeated except that benzyl bromide was replaced by m-methylbenzyl bromide [m-$CH_3C_6H_4CH_2Br$].

Ethyl m-methylphenylacetate [m-$CH_3C_6H_4CH_2COOC_2H_5$] was obtained.

EXAMPLE 6

The procedure of Example 1 was repeated except that benzyl bromide was replaced by o-methylbenzyl bromide [o-$CH_3C_6H_4CH_2Br$].

Ethyl o-methylphenylacetate [o-$CH_3C_6H_4CH_2COOC_2H_5$] was obtained.

EXAMPLE 7

The procedure of Example 1 was repeated except that benzyl bromide was replaced by p-fluorobenzyl bromide [p-$FC_6H_4CH_2Br$].

Ethyl p-fluorophenylacetate was obtained in 65% yield.

EXAMPLE 8

The procedure of Example 1 was repeated except that benzyl bromide was replaced by 2-bromomethylnaphthalene.

Ethyl 2-naphthylacetate [2-$NpCH_2COOC_2H_5$] was obtained in 70% yield.

EXAMPLE 9

The procedure of Example 8 was repeated except that $Al(OC_2H_5)_3$ was replaced by $Al[OCH(CH_3)_2]_3$.

Isopropyl 2-naphthylacetate [2-$NpCH_2COOCH(CH_3)_2$] was obtained in 50% yield.

EXAMPLE 10

The procedure of Example 8 was repeated except that $Al(OC_2H_5)_3$ was replaced by $Al[OCH(CH_3)_2C_2H_5]$.

Sec-butyl 2-naphthylacetate [2-$NpCH_2COOCH(CH_3)C_2H_5$] was obtained in 91% yield.

EXAMPLE 11

The procedure of Example 1 was repeated except that benzyl bromide was replaced by 1-bromomethylnaphthalene and $Pd(PPh_3)_4$(0.130 g;0.11 mmol) was added to the mixture.

Ethyl 1-methylnaphthylacetate [1-$NpCH_2COOC_2H_5$] was obtained in 78% yield.

EXAMPLE 12

The procedure of Example 11 was repeated except that $Al(OC_2H_5)_3$ was replaced by $Al[OCH(CH_3)_2]_3$.

Isopropyl 1-methylnaphthylacetate [1-$NpCH_2COOCH(CH_3)_2$] was obtained in 60% yield.

EXAMPLE 13

The procedure of Example 11 was repeated except that 1-bromomethylnaphthalene was replaced by bromobenzene.

Ethylbenzoate [$PhCOOC_2H_5$] was obtained in 80% yield.

EXAMPLE 14

The procedure of Example 1 was repeated except that benzyl bromide was replaced by beta-bromostyrene.

$PhCH=CHCOOC_2H_5$ was obtained in 25% yield.

EXAMPLE 15

The procedure of Example 11 was repeated except that 1-bromomethylnaphthalene was replaced by beta-bromostyrene.

$PhCH=CHCOOC_2H_5$ was obtained in 56% yield.

EXAMPLE 16

A mixture of 1,5-hexadienerhodium (I) chloride dimer (0.090 g; 0.11 mmol), $B(OC_2H_5)_3$ (2 ml) and benzyl bromide [$PhCH_2Br$] (2.0 mmol) was heated at 75° C. for about 15 hours under carbon monoxide. The solution was then cooled. Ether (10 ml) and 1M NaOH (5 ml) were added and the resulting mixture was filtered through Celite. The filtrate was extracted three times with ether (in total 250 ml), the ether extract was dried over anhydrous magnesium sulphate and the ester product recovered.

Ethyl phenylacetate [$PhCH_2COOC_2H_5$] was obtained in 100% yield.

EXAMPLE 17

The procedure of Example 16 was repeated except that p-methyl benzyl bromide [p-$CH_3C_6H_4CH_2Br$] was used instead of benzyl bromide.

Ethyl p-methylphenylacetate [p-$CH_3C_6H_4CH_2COOC_2H_5$] was obtained in 100% yield.

EXAMPLE 18

The procedure of Example 16 was repeated except that m-methyl benzyl bromide [m-$CH_3C_6H_4CH_2Br$] was used instead of benzyl bromide.

Ethyl m-methylphenylacetate [m-$CH_2C_6H_4CH_2COOC_2H_5$] was obtained in 100% yield.

EXAMPLE 19

The procedure of Example 18 was repeated except that $B(On-C_3H_7)_3$ was used instead of $B(OC_2H_5)_3$.

n-Propyl m-methylphenylacetate [m-$CH_3C_6H_4CH_2COOCH_2.CH_2.CH_3$] was abtained in 100% yield.

EXAMPLE 20

The procedure of Example 18 was repeated except that B (O.n-$C_4H_9$)$_3$ was used instead of $B(OC_2H_5)_3$.

n-Butyl m-methylphenylacetate [m-$CH_3C_6H_4CH_2COOCH_2.CH_2.CH_2.CH_3$] was obtained in 86% yield.

EXAMPLE 21

The procedure of Example 18 was repeated except that B (O.i-$C_3H_7$)$_3$ was used instead of $B(OC_2H_5)_3$ Isopropyl m-methylphenylacetate [m-$CH_3C_6H_4CH_2COOCH(CH_3)CH_3$] was obtained in 93% yield.

EXAMPLE 22

The procedure of Example 18 was repeated except that $B(Ot-C_4H_9)$ was used instead of $B(OC_2H_5)_3$.

t-Butyl m-methylphenylacetate [m-CH$_3$C$_6$H$_4$CH$_2$COOC(CH$_3$)$_3$] was obtained in 100% yield.

EXAMPLE 23

The procedure of Example 16 was repeated except that banzyl bromide was replaced by ortho-bromobenzyl bromide.
Ethyl o-bromophenylacetate [o-BrC$_6$H$_4$CH$_2$COOC$_2$H$_5$] was obtained in 90% yield.

EXAMPLE 24

The procedure of Example 23 was repeated except that B(OC$_2$H$_5$)$_3$ was replaced by B(On-C$_3$H$_7$)$_3$.
n-Propyl o-bromophenylacetate [o-BrC$_6$H$_4$CH$_2$COOCH$_2$CH$_2$CH$_3$] was obtained in 59% yield.

EXAMPLE 25

The procedure of Example 23 was repeated except that benzyl bromide was replaced by 2-bromomethyl naphthalene and Pd(PPh$_3$)$_4$(0.130 g; 0.11 mmol) was added to the mixture.
Ethyl 2-naphthylacetate [2-NpCH$_2$COOC$_2$H$_5$] was obtained in 90% yield.

EXAMPLE 26

The procedure of Example 16 was repeated except that B(OC$_3$H$_7$)$_3$ was used instead of B(OC$_2$H$_5$)$_3$.
n-Propyl 2-naphthylacetatee [2-NpCH$_2$COOCH$_2$CH$_2$CH$_3$] was obtained in 100% yield.

EXAMPLE 27

The procedure of Example 26 was repeated except that B(On-C$_4$H$_9$)$_3$ was used instead of B(OC$_2$H$_5$)$_3$.

EXAMPLE 28

The procedure of Example 26 was repeated except that B(On-C$_4$H$_9$)$_3$ was used instead of B(OC$_2$H$_5$)$_3$.
2-Bromomethylnaphthyl propionate [2-NpCH$_2$COOCH$_2$CH$_2$CH$_2$CH$_3$] was obtained in 100% yield.

EXAMPLE 29

The procedure of Example 26 was repeated except that B(Ot-C$_4$H$_9$)$_3$ was used instead of B(OC$_2$H$_5$)$_3$.
t-Butyl 2-naphthylacetate [2-NpCH$_2$COOC(CH$_3$)$_3$] was obtained in 88% yield.

EXAMPLE 30

The procedure of Example 16 was repeated except that benzyl chloride was used in place of benzyl bromide, the temperature was increased to 120° C. and potassium iodide was added in an amount such that the ratio of Rh:KI was 2:1.
Ethyl phenylacetate [PhCH$_2$COOC$_2$H$_5$] was obtained in 71% yield.

EXAMPLE 31

The procedure of Example 20 was repeated except that benzyl chloride was used in place of m-methyl benzyl bromide, the temperature was increased to 120° C. and potassium iodide was added in an amount such that the ratio of Rh:KI was 2:1.
n-Butyl phenylacetate was obtained in 100% yield.

EXAMPLE 32

The procedure of Example 16 was repeated except that Si(OEt)$_4$ was used in place of B(OC$_2$H$_5$)$_3$.
Ethyl phenylacetate was obtained in 95% yield.

EXAMPLE 33

The procedure of Example 16 was repeated except that benzyl bromide was replaced by benzyl chloride and B(OC$_2$H$_5$)$_3$ was replaced by Ti(OC$_2$H$_5$)$_4$.
Ethyl phenylacetate (PhCH$_2$COOC$_2$H$_5$) and dibenzyl ketone [(PhCH$_2$)$_2$CO] were obtained in 68% and 30% yield respectively.

EXAMPLE 34

The procedure of Example 33 was repeated except that Ti(OC$_2$H$_5$)$_4$ was replaced by Ti(O-n-C$_4$H$_9$)$_4$.
n-Butyl phenylacetate (PhCH$_2$COOC$_4$H$_9$) was obtained in 100% yield.

EXAMPLE 35

The procedure of Example 33 was repeated except that Ti(OC$_2$H$_5$)$_4$ was replaced by Zr(OC$_2$H$_5$)$_4$.
Ethyl phenylacetate (PhCH$_2$COOC$_2$H$_5$) was obtained in 100% yield.

EXAMPLE 36

The procedure of Example 33 was repeated except that Ti(OC$_2$H$_5$)$_4$ was replaced by Zr(O.n-C$_3$H$_7$)$_4$.
n-Propyl phenylacetate (PhCH$_2$COOn-C$_3$H$_7$) and benzyl propyl ether were obtained in 90% and 10% yield respectively.

EXAMPLE 37

The procedure of Example 33 was repeated except that Ti(OC$_2$H$_5$)$_4$ was replaced by Zr(O.n-C$_4$H$_9$)$_4$
n-Butyl phenylacetate (PhCH$_2$COO.n-C$_4$H$_9$) and benzyl butyl ether (PhCH$_2$OC$_4$H$_9$) were obtained in 80% and 12% yield respectively.

EXAMPLE 38

The procedure of Example 16 was repeated except that benzyl bromide was replaced by o-methyl benzyl chloride and B(OC$_2$H$_5$)$_3$ was replaced by Ti(O.n-C$_4$H$_9$)$_4$.
n-Butyl o-methylphenylacetate (O-CH$_3$C$_6$H$_4$CH$_2$COO.n-C$_4$H$_9$) was obtained in 87% yield.

EXAMPLE 39

The procedure of Example 38 was repeated except that Ti(O.n-C$_4$H$_9$)$_4$ was replaced by Zr(O.n-C$_4$H$_9$)$_4$.
n-Butyl o-methylphenylacetate (O-CH$_3$C$_6$H$_4$CH$_2$COO.n-C$_4$H$_9$) and o-methylbenzyl n-butyl ether (o-CH$_3$C$_6$H$_4$CH$_2$O.n-C$_4$H$_9$) were obtained in 69% and 25% yield respectively.

EXAMPLE 40

The procedure of Example 30 was repeated except that benzyl chloride was replaced by m-methoxy benzyl chloride.
Ethyl m-methoxyphenylacetate was obtained in 100% yield.

EXAMPLE 41

The procedure of Example 40 was repeated except that B(OC$_2$H$_5$)$_3$ was replaced by B(O.t-C$_4$H$_9$)$_3$.

n-Butyl m-methoxyphenylacetate was obtained in 98% yield.

We claim:

1. A process for the production of a carboxyic acid ester which process comprises reacting (i) carbon monoxide, (ii) a compound of the formula $M(OR)_x$ wherein M is either boron, silicon, aluminium, titanium or zirconium, x is the valency of M and R is a hydrocarbyl group and (iii) a hydrocarbyl halide, wherein the halide moiety is bromide, chloride or iodide, in the presence of a catalyst comprising one or more of the metals rhodium, iridium and cobalt added in either elemental or compound form.

2. A process according to claim 1 wherein the hydrocarbyl group R in the formula $M(OR)_x$ is an alkyl group.

3. A process according to claim 2 wherein the alkyl group is a primary or secondary alkyl group.

4. A process according to claim 1 wherein M in the formula $M(OR)_x$ is boron, silicon or aluminium and the halide moiety of the hydrocarbyl halide is the bromide.

5. A process according to any one of claims 1 to 3 wherein M in the formula $M(OR)_x$ is titanium or zirconium and the halide moiety of the hydrocarbyl halide is the chloride, bromide or iodide.

6. A process according to any one of claims 1 to 3 wherein M in the formula $M(OR)_x$ is boron, silicon or aluminium, the halide moiety of the hydrocarbyl halide is chloride and there is added a source of iodide.

7. A process according to claim 5 wherein there is added a source of iodide.

8. A process according to either claim 6 or claim 7 wherein the source of iodide is either iodine, an inorganic iodide or an organic iodide.

9. A process according to claim 1 wherein the catalyst is a rhodium compound.

10. A process according to claim 1 wherein there is employed a bimetallic catalyst comprising one of the metals rhodium, iridium and cobalt and another metal selected from Group VIII of the Periodic Table of the elements.

11. A process acording to claim 10 wherein there is employed as one component of the bimetallic catalyst a metal in the form of a compound of a hydrocarbyl substituted phosphine, arsine or stibine.

12. A process according to either claim 10 or claim 11 wherein the bimetallic catayst is employed when a hydrocarbyl halide which is an aromatic halide is a reactant.

13. A process according to claim 1 wherein the reaction temperature is in the range 50° to 150° C.

* * * * *